(12) United States Patent
Diehl et al.

(10) Patent No.: US 6,242,647 B1
(45) Date of Patent: Jun. 5, 2001

(54) INSECTICIDAL BIPHENYLTHIOHYDRAZIDES

(75) Inventors: Robert Eugene Diehl, Yardley; David Allen Hunt, Newtown; Susan Hensen Trotto, Yardley, all of PA (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/204,568

(22) Filed: Dec. 3, 1998

(51) Int. Cl.[7] .................................................. C07C 241/00
(52) U.S. Cl. ............................ 564/251; 564/74; 514/599; 514/602
(58) Field of Search ..................... 564/251, 74; 514/599, 514/600

(56) References Cited

U.S. PATENT DOCUMENTS 5,556,885   9/1996   Trotto et al. ......................... 514/639

FOREIGN PATENT DOCUMENTS

417626 A2   3/1991   (EP) .
WO 93/10083   5/1993   (WO) ........................... C07C/281/02

*Primary Examiner*—Paul J. Killos
(74) *Attorney, Agent, or Firm*—Barbara L. Renda; Barbara V. Maurer

(57) ABSTRACT

The present invention provides N-biphenylthiohydrazone derivatives of formula I

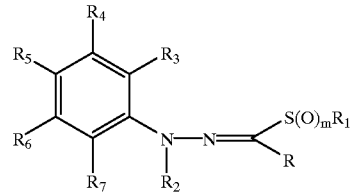

and compositions and methods for the use thereof in the control of insect and acarid pests and for the protection of crops therefrom.

18 Claims, No Drawings

INSECTICIDAL BIPHENYLTHIOHYDRAZIDES

BACKGROUND OF THE INVENTION

Significant global economic losses in major agronomic crop production are caused by the damage and infestation of insect and acarid pests. Crop reduction due to said pests, for example, in cotton and peanuts, can range as high as 39% and 78%, respectively. Pest infestation can result in lower yields, lower crop quality, reduced consumption, increased perishability, increased risk of disease, higher processing cost, higher transportation cost and increased market prices. Therefore, new and effective insect and acarid control agents and crop protection methods are a continuing global need.

It is thus an object of this invention to provide N-biphenylthiohydrazone derivatives which are effective agents for the control of pestiferous insects and especially, acarina.

It is another object of this invention to provide a method for the protection of growing and harvested crops from the harmful and deleterious effects caused by insects and especially, acarid pests.

It is a further object of this invention to provide insecticidal and acaricidal compositions for use in the methods of the invention.

SUMMARY OF THE INVENTION

The present invention provides novel N-biphenylhydrazone compounds of formula I

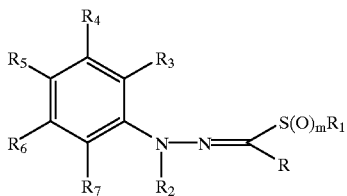

(I)

wherein
R is hydrogen,
  $C_1$–$C_{10}$alkyl optionally substituted with one or more halogen,
  $C_3$–$C_6$cycloalkyl,
  $C_1$–$C_4$alkoxy,
  $C_1$–$C_4$haloalkoxy,
  ($C_1$–$C_4$-alkyl)$SO_x$,
  ($C_1$–$C_4$haloalkyl)$SO_y$,
  phenyl optionally substituted with one to three halogen,
    $C_1$–$C_4$alkyl,
    $C_1$–$C_4$haloalkyl,
    $C_1$–$C_4$alkoxy,
    $C_1$–$C_4$haloalkoxy,
    ($C_1$–$C_4$alkyl)$SO_x$,
    ($C_1$–$C_4$haloalkyl)$SO_y$,
    $NO_2$ or CN groups, or
  phenoxy optionally substituted with one to three halogen,
    $C_1$–$C_4$alkyl,
    $C_1$–$C_4$haloalkyl,
    $C_1$–$C_4$alkoxy,
    $C_1$–$C_4$haloalkoxy,
    ($C_1$–$C_4$alkyl)$SO_x$,
    ($C_1$–$C_4$haloalkyl)$SO_y$,
    $NO_2$ or CN groups;
  $C_3$–$C_{12}$cycloalkyl optionally substituted with one or more halogens,
    $C_1$–$C_6$alkyl,
    $C_1$–$C_4$haloalkyl,
    $C_1$–$C_4$alkoxy,
    $C_1$–$C_4$haloalkoxy,
    ($C_1$–$C_4$alkyl)$SO_x$,
    ($C_1$–$C_4$haloalkyl)$SO_x$,
  phenyl optionally substituted with one to three halogen,
    $C_1$–$C_4$alkyl
    $C_1$–$C_4$haloalkyl,
    $C_1$–$C_4$alkoxy,
    $C_1$–$C_4$haloalkoxy,
    $NO_2$ or CN groups, or
  phenoxy optionally substituted with one to three halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups; or
  phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups;
with the proviso that when R is phenyl, then m must be 1 or 2;
$R_1$ is $R_{12}$,
  $C_1$–$C_{10}$alkyl optionally substituted with one or more halogen,
  hydroxy,
  phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups,
  $C_1$–$C_4$alkoxy,
  $C_1$–$C_4$haloalkoxy,
  ($C_1$–$C_4$alkyl)$SO_x$,
  $CONR_8R_9$,
  $CO_2R_{10}$,
  $R_{12}$,
  $C_3$–$C_6$cycloalkyl optionally substituted with one to three halogen,
    $C_1$–$C_4$alkyl,
    $C_1$–$C_4$ haloalkyl,
    $C_1$–$C_4$alkoxy,
    $C_1$–$C_4$haloalkoxy,
    $NO_2$ or CN groups,
  phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
  pyridyl optionally substituted with one or more halogen,
    $C_1$–$C_4$alkyl,
    $C_1$–$C_4$haloalkyl,
    $C_1$–$C_4$alkoxy, $C_1$–$C_4$haloalkoxy,
$NO_2$ or CN groups;
$C_2$–$C_{10}$alkenyl optionally substituted with one or more halogen,
hydroxy,
$C_1$–$C_4$alkoxy,
$C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$C_2$–$C_{10}$alkynyl optionally substituted with one or more halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups; or
$C_3$–$C_{12}$cycloalkyl optionally substituted with one or more halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$R_2$ is hydrogen or $C_1$–$C_4$alkyl;
$R_3$, $R_4$, $R_5$, $R_6$, and $R_7$ are each independently hydrogen, halogen, CN, $NO_2$, $C_1$–$C_6$alkyl, $C_1$–$C_6$haloalkyl, $C_1$–$C_6$alkoxy, $C_1$–$C_6$haloalkoxy, or phenyl optionally substituted with one to three halogen, $C_1$–$C_4$alkyl, $C_1$–$C_4$haloalkyl, $C_1$–$C_4$alkoxy, $C_1$–$C_4$haloalkoxy, ($C_1$–$C_4$alkyl)$SO_x$, ($C_1$–$C_4$haloalkyl)$SO_y$, $NO_2$ or CN groups,
with the proviso that at least one of $R_3$, $R_4$, $R_5$, $R_6$ or $R_7$ must be phenyl optionally substituted with one to three halogen, $C_1$–$C_4$alkyl, $C_1$–$C_4$haloalkyl, $C_1$–$C_4$alkoxy, $C_1$–$C_4$haloalkoxy, ($C_1$–$C_4$alkyl)$SO_x$, ($C_1$–$C_4$haloalkyl) $SO_x$, $NO_2$ or CN groups;
x and y are each independently 0, 1 or 2;
m is an integer of 0, 1 or 2;
$R_8$, $R_9$ and $R_{10}$ are each independently hydrogen or $C_1$–$C_4$alkyl;
$R_{11}$ is $NR_{13}R_{14}$,

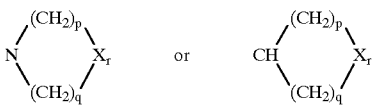

$R_{12}$ is

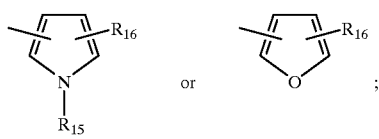

or $R_{13}$, $R_{14}$, and $R_{15}$ are each independently hydrogen or $C_1$–$C_4$alkyl;
X is O, S or $NR_{15}$;
$R_{16}$ is hydrogen, halogen or $C_1$–$C_4$ alkyl;
r is an integer of 0 or 1;
p and q are each independently an integer of 0, 1, 2, or 3 with the proviso that only one of p, q, or r can be 0 and with the further proviso that the sum of p+q+r must be 4, 5 or 6; and
x is an integer of 0, 1 or 2; or
the acid addition salts thereof.

Also provided are methods and compositions for the control of insect and acarid pests and for the protection of growing and harvested crops from attack and infestation thereby.

DETAILED DESCRIPTION OF THE INVENTION

A wide variety of insects and acarina cause great economic loss by damaging or destroying agricultural crops and horticultural and pharmaceutical plants; by aiding in the spread and development of bacteria, fungi and viruses that produce diseases of plants; and by destroying or lowering the value of stored foods, other products and possessions. Insect and acarid attack and infestation cause some of the farmers' greatest problems the world over. The need for alternative and effective insect and acarid control is a global concern.

It has now been found that the N-biphenylthiohydrazone compounds of formula I are highly effective agents for the control of a wide variety of insect and, particularly, acarid pests. As such, these compounds can be used to advantage to combat mites of the species *Tetranychus uriticae* (Koch). Moreover, compounds of the present invention have been found to exhibit good activity against mite species which have developed resistance to existing commercial acaricides.

Advantageously, compounds of formula I not only possess acaricidal activity but also exhibit useful activity against insect pests including *Spodoptera eridania*, southern army worms; *Diabrotica virgifera*, western corn rootworms; *Heliothis virescens*, tobacco budworms; *Aphis fabae*, bean aphids, and *Aphis gossypii*, cotton aphids.

Preferred compounds of the invention are those compounds of formula I wherein $R_4$ and $R_6$ are each independently H or phenyl optionally substituted with one or more halogen, $C_1$–$C_4$haloalkoxy, or $C_1$–$C_4$haloalkyl groups. More preferred compounds of the invention are those formula I compounds wherein R is $C_1$–$C_6$alkyl or $C_3$–$C_6$cycloalkyl optionally substituted with one to three halogens; $R_3$ and $R_7$ are each independently H or $C_1$–$C_6$alkoxy; and $R_4$ and $R_6$ are each independently H or phenyl optionally substituted with one or more halogen, $C_1$–$C_4$haloalkoxy or $C_1$–$C_4$haloalkyl groups.

The term "halogen" as used herein denotes chlorine, fluorine, bromine or iodine. The term "haloalkyl" notes an alkyl group, $C_nH_{2n+1}$, which contains from one halogen atom to 2n+1 halogen atoms. Similarly, the term "haloalkoxy" denotes a $OC_nH_{2n+1}$ group which contains from one to 2n+1 halogen atoms. The halogen atoms may be the same or different.

The term "acid addition salts" denotes those salts formed by acids commonly known in the art such as hydrogen chloride, hydrogen bromide, hydrogen bisulfate, hemi-hydrogen sulfate and the like.

In the above definition of formula I, when n is 0, then Y is hydrogen.

Those compounds of formula I wherein m is an integer of 1 or 2 may be prepared by the oxidation of the appropriate precursor using standard oxidizing reagents such as m-chloroperbenzoic acid (mcpba), hydrogen peroxide and acetic acid, $KMnO_4$, and the like in accordance with standard known reaction conditions, for instance, those described in U.S. Pat. No. 5,556,885. Typically this reaction is conducted at room temperature for periods of 1–4 days in a suitable solvent such as methylene chloride. This reaction is shown below flow diagram I.

Flow Diagram I

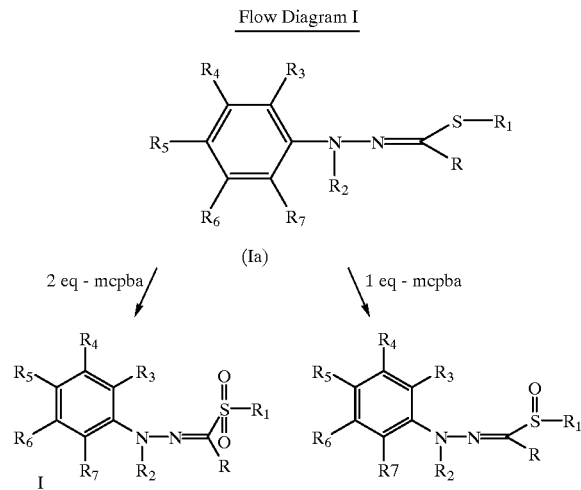

These compounds of formula I wherein m is 0 may be prepared by reacting the appropriate hydrazinoyl halide of formula II wherein $X^1$ is halogen with a suitable mercaptan of formula III wherein $R_1$ is as hereinbefore defined in the presence of a base as shown below in flow diagram II.

Flow Diagram II

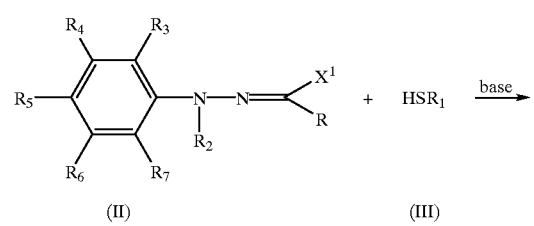

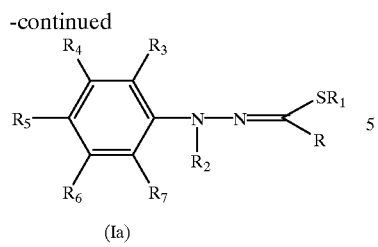

(Ia)

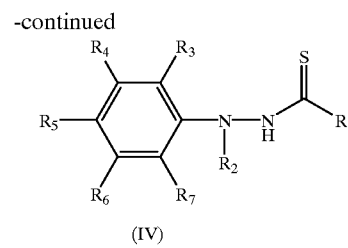

(IV)

Alternatively, the appropriate N-biphenylthiohydrazide of formula IV may be reacted with the appropriate alkyl halide in the presence of a suitable base to give the desired N-biphenylthiohydrazone compounds of formula Ia. The base utilized can be either organic or inorganic, and typically is sodium or potassium carbonate. Suitable solvents include those such as acetone, and typically the reaction is conducted at reflux temperature thereof for periods of about ½ to 4 hours. This reaction is illustrated below in flow diagram III.

Flow Diagram III

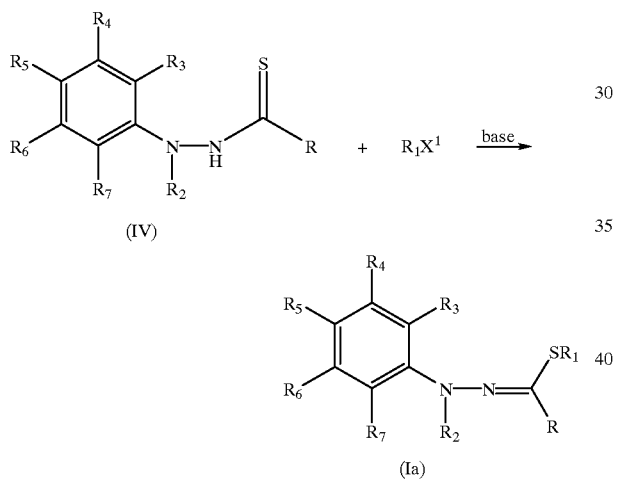

Compounds of formula IV may be readily prepared by the reaction of the corresponding biphenyl hydrazide of formula V with Lawesson's Reagent. Typically, this reaction is conducted in a suitable solvent, such as toluene or benzene, at temperatures ranging from about 50° C. to about 80° for a period of about ½ to 4 hours. The reaction scheme is shown in flow diagram IV.

Flow Diagram IV

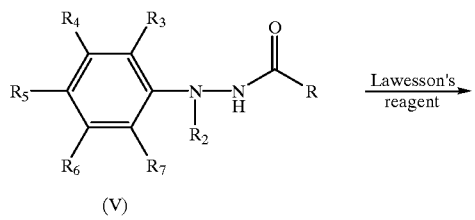

Compounds of formula II may be prepared by reacting triphenylphosphine and carbon tetrachloride with the corresponding biphenyl hydrazide of formula V. Alternatively, the formula II compound may be prepared by heating the appropriate formula V biphenyl hydrazide with phosphorus pentachloride, and treating the reaction mixture sequentially with carbon tetrachloride and phenol. These reactions are illustrated below in flow diagram V.

Flow Diagram V

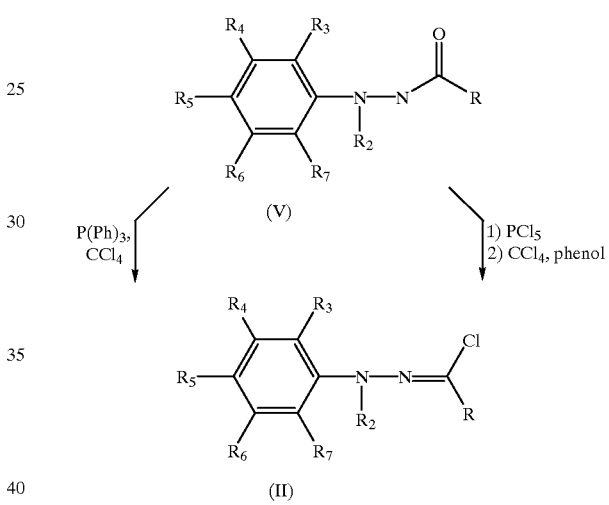

Further, formula II compounds may be prepared using conventional literature methods such as those described by Tanaka Kiyoshi, Maeno Seiji, and Mitsuhashi Keiryo in the Journal of Heterocyclic Chemistry, 22 (1985), pp. 565–568.

Similarly, compounds of formula V may be readily prepared by conventional methods such as those described in WO 93/10083.

Growing or harvested crops may be protected from attack or infestation by insect or, particularly, acarid pests by applying to the foliage of the crops, or to the soil or water in which they are growing, a pesticidally effective amount of N-biphenylthiohydrazone derivative of formula I.

In actual agronomic practice, generally about 10 ppm to 10,000 ppm, and preferably about 100 to 5,000 ppm, of the formula I compound is dispersed in a liquid carrier. When applied to the plants or the soil or water in which they are growing, these amounts are effective to protect the plants from insect and acarina attack and infestation. Applications, such as spray applications, of compositions of the invention are generally effective at rates which provide about 0.125 kg/ha to about 250 kg/ha, preferably about 10 kg/ha to 100 kg/ha of active ingredient. The rate of application may be dependent upon the prevailing environmental circumstances such as population density, degree of infestation, stage of plant growth, soil conditions, weather conditions and the like.

Advantageously, the formula I compounds may be used in conjunction with, or in combination with, other biological and chemical control agents including insecticides, nematicides, acaricides, molluscicides, and fungicides. Insecticides may include nuclear polyhedrosis viruses, pyrroles, arylpyrroles, halobenzoylureas, pyrethroids, carbamates, phosphates, and similar conventional insect agents.

Typical formulations suitable for the formula I N-biphenylthiohydrazone derivatives are sprays, granular compositions, flowable compositions, wettable powders, dusts, microemulsions, emulsifiable concentrates or any conventional agricultural composition. All compositions which lend themselves to soil, water and foliage application and provide effective plant protection are suitable. Compositions of the invention include the I N-biphenylthiohydrazone derivative of formula I admixed with an agriculturally acceptable solid or liquid carrier.

Where compositions of the invention are to be employed in combination treatments with other biological or chemical agents, the composition may be applied as an admixture of the components or may be applied sequentially to the target pest and/or crop. While not required, the combination composition comprising a formula I compound and a co-pesticide may also comprise other components, for example, fertilizers, inert formulation aides such as surfactants, emulsifiers, defoamers, dyes, extenders and the like.

In order to aid in the understanding of the invention, specific examples thereof are set forth below. The invention described and claimed herein is not to be limited in scope by these merely illustrative examples. Indeed, various modifications of the invention in addition to those exemplified and described herein will become apparent to those skilled in the art from the following examples and the foregoing description. Such modifications are also intended to fall within the scope of the appended claims.

The terms $^1$H, $^{13}$C, $^{19}$F NMR designate proton, carbon and fluorine nuclear magnetic resonance spectroscopy, respectively. IR designates infrared spectroscopy.

EXAMPLE 1

Preparation of (4-Methoxy -3-biphenylyl)hydrazine Hydrochloride

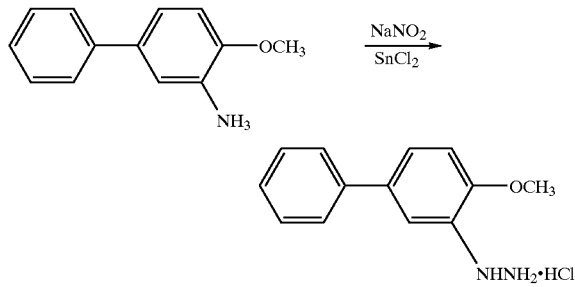

A suspension of 5-phenyl-o-anisidine (10 g, 50.0 mmol) in water and hydrochloric acid (concentrated, 180 ml) is cooled to 0° C., treated dropwise with a 0° C. solution of sodium nitrite (3.45 g, 50.0 mmol) in water, stirred for one hour, treated with a −20° C. solution of tin chloride (45.2 g, 238 mmol) in concentrated hydrochloric acid (80 ml), stirred for one hour at 0° C. and filtered. The filter cake is mixed with hot water and filtered. The filtrate is cooled and filtered to obtain the title product, as beige crystals, in 64.3% yield, mp 184–186° C.

EXAMPLE 2

Preparation of 2,2-Dimethylpropionate, 2-(4-Methoxy-3-biphenylyl)hydrazide

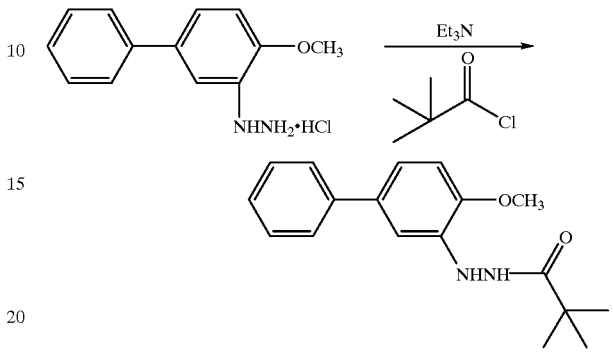

A suspension of (4-methoxy-3-biphenylyl)hydrazine, hydrochloride (25.07 g, 100 mmol) in methylene chloride is treated with triethylamine (21.25 g, 210 mmol). A solution of trimethylacetyl chloride (12.06 g,100 mmol) in methylene chloride is added dropwise to the reaction mixture and stirred for four hours at room temperature. After pouring the reaction mixture into water, the mixture is extracted with ethyl acetate, and the extract washed with 15% hydrochloric acid, water, and a saturated aqueous solution of sodium chloride, dried over sodium sulfate and filtered. The filtrate is concentrated in vacuo and the resultant pink residue recrystallized from hexane to afford the title product, as a white solid (21.7 g), in 75.5% yield, mp 153–156° C. Identity is confirmed by $^1$HNMR, $^{13}$CNMR, and IR.

EXAMPLE 3

Preparation of 1-Chloro-2,2-dimethylpropionaldehyde, 2-(4-Methoxy-3-biphenylyl)hydrazone

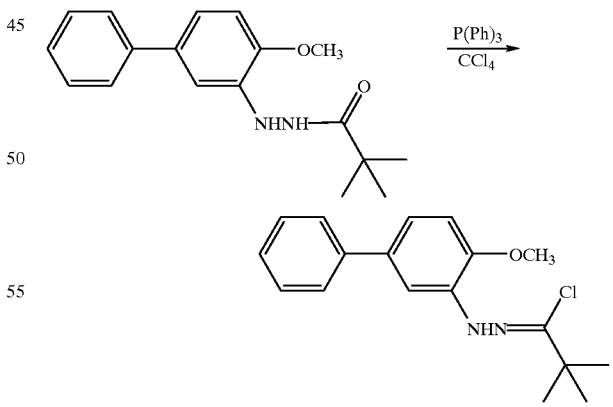

A solution of 2,2-dimethylpropionate, 2-(4-methoxy-3-biphenylyl)hydrazide (5.97 g, 20 mmol) and triphenylphosphine (15.7 g, 60 mmol) in acetonitrile is treated with carbon tetrachloride (10.15 g, 66 mmol), stirred for one hour and concentrated in vacuo to afford an orange residue. The residue is dissolved in ether, cooled to −32° C. and filtered.

The filtrate is concentrated in vacuo to afford the title product, as a white solid (3.53 g), in 55.7% yield. Identity is confirmed by ¹HNMR and ¹³CNMR.

EXAMPLE 4

Preparation of 1-Chloro-2,2-dimethylpropionaldehyde, 2-(4-Methoxy-3-biphenylyl)hydrazone

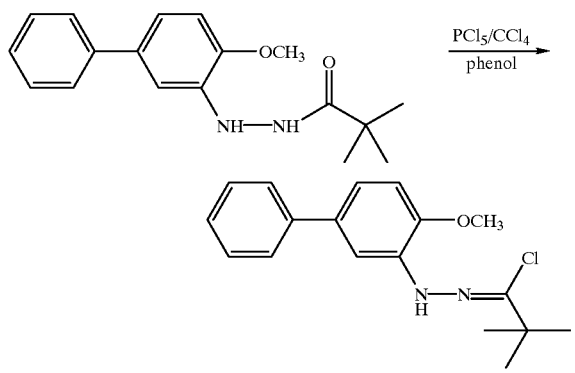

A suspension of 2,2-dimethylpropionate, 2-(4-methoxy-3-biphenylyl)hydrazide (7.46 g, 25 mmol) and phosphorus pentachloride (5.47 g, 26 mmol) in carbon tetrachloride is refluxed for 15 minutes. The reaction mixture is cooled to 0° C., treated with phenol (7.9 g, 84 mmol), warmed to room temperature and concentrated in vacuo give a brown oil. The oil is recrystallized from hexane to afford the title product, as a beige solid (4.66 g), in 58.9% yield. Identity is confirmed by ¹HNMR, ³CNMR, and IR.

EXAMPLE 5

Preparation of S-Methyl 2,2-Dimethylthiopropionate, (4-Methoxy-3-biphenylyl)hydrazone

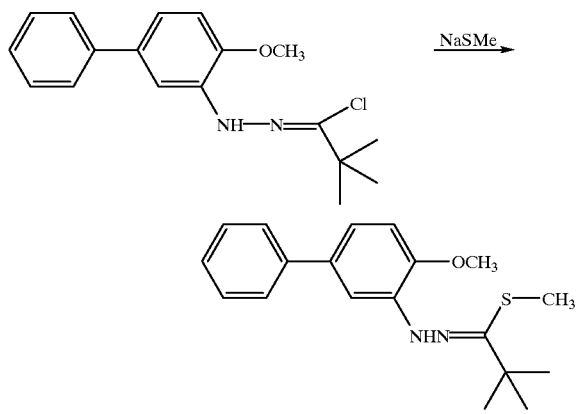

A solution of sodium thiomethoxide (1.12 g, 16 mmol) in methylene chloride (150 ml) is treated with 1-chloro-2,2-dimethylpropionaldehyde, 2-(4-methoxy-3-biphenylyl)hydrazone (4.6 g, 14.5 mmol) and stirred for several hours at room temperature. The reaction mixture is poured into water extracted with methylene chloride. The extract is washed with dilute aqueous sodium hydroxide solution, water, and aqueous saturated sodium chloride, then dried over magnesium sulfate and filtered. After concentration of the filtrate in vacuo, the resultant yellow residue is dissolved in hexane and filtered. The filtrate is concentrated in vacuo to afford the title product, as a yellow oil (3.7 g), in 77.7% yield. Identity is confirmed by ¹HNMR, ¹³CNMR, and IR.

EXAMPLE 6

Preparation of 2,2-Dimethylthiopropionate, 2-(5-Fluoro-4-methoxy-3-biphenylyl)hydrazide

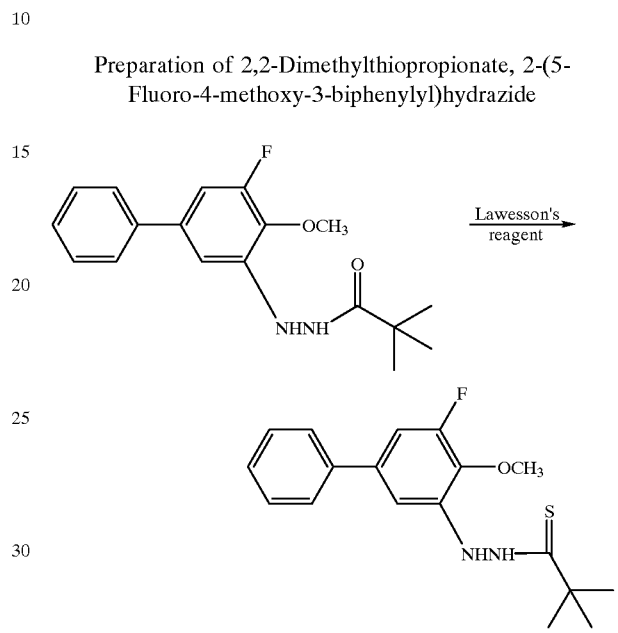

Lawesson's reagent (4.14 g, 103 mmol) is added to a solution of 2,2-dimethylthiopropionate, 2-(5-fluoro-4-methoxy-3-biphenylyl)hydrazide (6.33 g, 20 mmol) in toluene and the reaction mixture heated to 80° C. After approximately three hours at 80° C., the reaction mixture is cooled to room temperature and filtered. The filtrate is concentrated in vacuo to give an oily residue which was purified by silica gel flash chromatography. The title product is obtained, as a white solid (4.1 g) in 61.7% yield, mp 96–97° C. Identity is confirmed by ¹HNMR, ¹³CNMR, and IR.

EXAMPLE 7

Preparation of S-Methyl 2,2-Dimethylthiopropionate, 2-(5-Fluoro-4-methoxy-3-biphenylyl)hydrazone

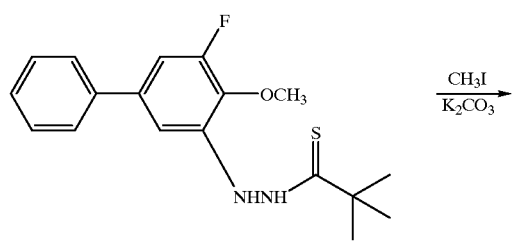

-continued

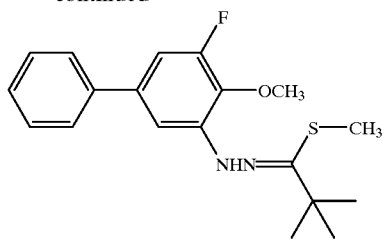

Methyl iodide (0.78 g, 5.5 mmol) is added slowly to a suspension of 2,2-dimethylthiopropionate-,2-(5-fluoro-4-methoxy-3-biphenylyl)hydrazide (1.6 g, 5 mmol) and potassium carbonate (0.76 g, 5.5 mmol) in acetone at reflux. After three hours, the reaction mixture is cooled, poured into water, and extracted with ethyl acetate. The extract is washed with water and saturated aqueous sodium chloride solution, dried over sodium sulfate and filtered. The filtrate is concentrated in vacuo to afford the title product as a yellow oil, (1.7 g) in 98.3% yield. Identity is confirmed by $^1$HNMR, $^{13}$CNMR, and IR.

EXAMPLES 8–14

Preparation of the N-Biphenylthiohydrazone Compounds

Using essentially the same procedures described in Examples 1–7, and substituting the appropriate reagents, the compounds specified in the following Table I are prepared. The compounds obtained are oils, except where indicated, and their identity is confirmed by $^1$HNMR, $^{13}$CNMR, IR, mass spectral and elemental analyses.

EXAMPLE 15

Preparation of S-Methyl 2,2-Dimethylthiopropionate, 2-(4-Methoxy-3-biphenylyl)hydrazone, S,S-Dioxide

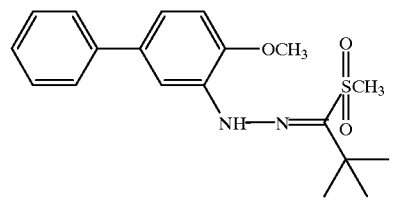

A solution of S-methyl 2,2-dimethylthiopropionate, (4-methoxy-3-biphenylyl)hydrazone (1.2 g, 3.9 mmol) in methylene chloride is treated dropwise with m-chloroperbenzoic acid (1.3 g, 8.1 mmol) and stirred for 3 days at room temperature. The reaction mixture is then poured into water extracted with methylene chloride and the extract washed with an aqueous solution of potassium carbonate (10%), water, a saturated aqueous solution of sodium chloride, and then dried over magnesium sulfate and filtered. The filtrate is concentrated in vacuo to afford an oil which is purified via flash chromatography on silica gel. The title product is obtained, as a white solid (0.5 g) in 35.5% yield, mp 134–136° C. Identity is confirmed by $^1$HNMR, $^{13}$CNMR, IR and C, H, and N elemental analyses.

TABLE I

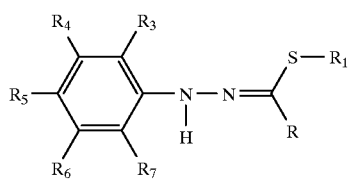

| Exp No. | $R_7$ | $R_6$ | $R_5$ | $R_4$ | $R_3$ | $R_1$ | R | yield (%) | mp. (° C.) |
|---|---|---|---|---|---|---|---|---|---|
| 8 | H | H | H | H | $C_6H_5$ | $CH_3$ | $C(CH_3)_3$ | 77.3 | oil |
| 9 | H | H | H | H | $C_6H_5$ | $CH_3$ | 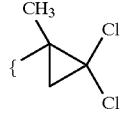 | 83.3 | oil |
| 10 | H | H | $C_6H_5$ | H | H | $CH_3$ | $C(CH_3)_3$ | 13.8 | oil |
| 11 | H | H | H | H | $pCF_3$—$C_6H_4$ | $CH_3$ | $C(CH_3)_3$ | 59 | 60–62 |
| 12 | H | H | $OCF_3$ | H | $C_6H_5$ | $C_2H_5$ | $C(CH_3)_3$ | 77 | 50–52 |
| 13 | H | H | H | $pCF_3$—$C_6H_4$ | H | $CH_3$ | $C(CH_3)_3$ | 79.5 | 55–58 |
| 14 | H | H | $C_6H_5$ | $CF_3$ | H | $CH_3$ | $C(CH_3)_3$ | 98 | oil |

EXAMPLES 16–22

Preparation of N-Biphenylthiohydrazone S,S-Dioxide Compounds

Using essentially the same procedure described in Example 15, and substituting the appropriate reagents, the following compounds specified in Table II are prepared. The compounds obtained are oils, except where indicated, and their identity is confirmed by $^1$HNMR, $^3$CNMR, IR, mass spectral and elemental analyses.

perature. After adding methylene chloride, the reaction mixture is then washed with potassium carbonate (10%), water, and a saturated aqueous solution of sodium chloride. After drying over magnesium sulfate and filtering, the filtrate is concentrated in vacuo to afford an oil which is purified via silica gel flash chromatography. The title product is obtained, as an orange solid (0.09 g), in 15% yield, mp 139–140° C. Identity is confirmed by $^1$HNMR, $^{13}$CNMR, IR and C, H, and N elemental analyses.

TABLE II

| Exp. No. | R$_7$ | R$_6$ | R$_5$ | R$_4$ | R$_3$ | R$_1$ | R | yield (%) | mp. (° C.) |
|---|---|---|---|---|---|---|---|---|---|
| 16 | H | H | H | H | C$_6$H$_5$ | —CH$_3$ | (1,1-dichloro-2-methylcyclopropyl) | 20.2 | oil |
| 17 | H | H | H | H | C$_6$H$_5$ | —CH$_3$ | C(CH$_3$)$_3$ | 38.3 | 97–100 |
| 18 | H | H | H | H | pCF$_3$—C$_6$H$_4$ | —CH$_3$ | C(CH$_3$)$_3$ | 33 | 122–124 |
| 19 | H | H | H | C$_6$H$_5$ | H | —CH$_3$ | C(CH$_3$)$_3$ | 66.7 | 119–121 |
| 20 | Cl | H | C$_6$H$_5$ | H | Cl | —CH$_3$ | C(CH$_3$)$_3$ | 100 | 145–148 |
| 21 | H | C$_6$H$_5$ | H | F | OCH$_3$ | CH$_3$ | C(CH$_3$)$_3$ | 37.7 | 98–101 |
| 22 | H | pCF$_3$—C$_6$H$_4$ | H | H | H | CH$_3$ | C(CH$_3$)$_3$ | 15.4 | 155–160 |

EXAMPLE 23

Preparation of S-Methyl 2,2-Dimethylthiopropionate, 2-[4'-(Trifluoromethyl)-2-biphenylyl]hydrazone, S-Oxide

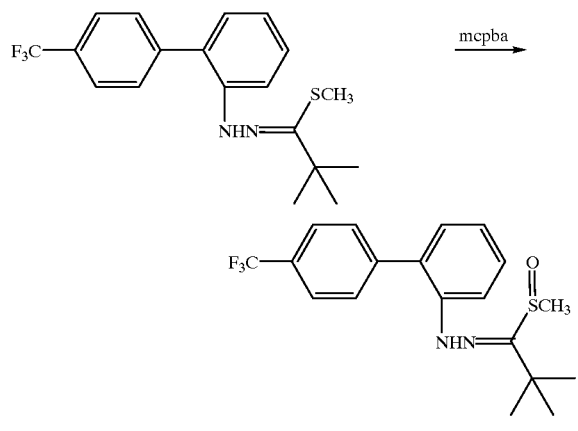

A solution of S-methyl 2,2-dimethylthiopropionate 2-[4' (trifluoromethyl)-2-biphenylyl]hydrazone (1.2 g, 3.9 mmol) in methylene chloride is treated with 3-chloroperbenzoic acid (1.3 g, 8.1 mole) and stirred overnight at room tem-

EXAMPLE 24

Insecticidal Evaluation of N-Biphenylthiohydrazone, S-Methyl Esters, and S-Oxide, and S,S-Dioxide Compounds In these evaluations, test solutions are prepared by dissolving the test compound in a 35% acetone in water mixture to give a concentration of 10,000 ppm (4,000 ppm for cotton aphids). Subsequent dilutions are made with water as needed.

*Spodoptera eridania,* 3rd Instar Larvae, Southern Armyworm (SAW)

A Sieva limabean leaf expanded to 7–8 cm in length is dipped in the test solution with agitation for 3 seconds and allowed to dry in a hood. The leaf is then placed in a 100×10 mm petri dish containing a damp filter paper on the bottom and ten 3rd instar caterpillars. At 5 days, observations are made of mortality, reduced feeding, or any interference with normal molting.

*Diabrotic virgifera vergifera Leconte,* 3rd Instar Western Corn Rootworm (WCR)

One cc of fine talc is placed in a 30 ml wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 ml of moist soil is added to each jar. The jar is capped and the contents thoroughly mixed on a Vortex Mixer. Following this, ten 3rd instar root-worms are added to each jar and the jars are loosely capped to allow air exchange for the larvae. The treatments are held for 5 days when mortality counts are made. Missing larvae are presumed dead, since they decompose rapidly and can not be found. The concentrations used in this test correspond approximately to 50 kg/ha.

*Heliothis virenscens*, 3rd Instar Tobacco Budworm (TBW)

Cotton cotyledons are dipped in the test solution and allowed to dry in a hood. When dry, each is cut into quarters and ten sections are placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Tetranychus urticae* (OP-Resistant Strain), 2-Spotted Spider Mite (TSM)

Sieva limabean plants with primary leaves expanded to 7–8 cm are selected and cut back to one plant per pot. A small piece is cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly mite-infested plants are dipped in the test solution for 3 seconds with agitiation and set in the hood to dry. After 2 days, one leaf is removed and mortality counts are made. After 5 days, another leaf is removed and observations are made of mortality of the eggs and/or newly emerged nymphs.

*Aphis fabae*. Mixed Instar, Bean Aphid (BA)

Pots containing single nasturtium plants (Tropaeolum sp.) about 5 cm tall are infested with about 100–200 aphids one day before the test. Each pot is sprayed with the test formulation for 2 revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and held for 2 days, following which mortality estimates are made.

*Aphis gossypii* (Cotton Aphid)

A heavily infested leaf is placed on top of a cotton plant which had been grown to the cotyledon stage. The aphids are allowed to transfer from the leaf section to the host plant overnight. The resultant infested leaves of the intact plant are dipped into the test solution and then allowed to dry. Aphid mortality counts are made after the test plants have been maintained under GRO-LUX® lights (24 hour photoperiod) at 27–28° C. for 5 days. Phytotoxicity to the cotton plant is also recorded at this time.

The tests are rated according to the scale shown below and the data obtained are shown in Table III. When more than one test is conducted, the results are averaged.

| RATING SCALE | | | |
|---|---|---|---|
| Rate | % Mortality | Rate | % Mortality |
| 0 | no effect | 5 | 56–65 |
| 1 | 10–25 | 6 | 66–75 |
| 2 | 26–35 | 7 | 76–85 |
| 3 | 36–45 | 8 | 86–99 |
| 4 | 46–55 | 9 | 100 |
| | | — | not tested |

TABLE III

Insecticidal Evaluation Of N-Biphenylthiohydrazone, S-oxide, and S,S-dioxide Compounds

| | % Mortality | | | | | |
|---|---|---|---|---|---|---|
| Compound (Ex. No.) | SAW 300 ppm | WCR (50 ppm) | TSM (300/50 ppm) | TBW (300 ppm) | BA (10 ppm) | CA (100 ppm) |
| 5 | 0 | 0 | 9/9 | 0 | 0 | 0 |
| 7 | 0 | 9 | 9/9 | 0 | 0 | 8 |
| 8 | 7 | 9 | 9/8 | 0 | 7 | 8 |
| 9 | — | 0 | 9/8 | 0 | 0 | 5 |
| 10 | 9 | 0 | 0/0 | — | 0 | 0 |
| 11 | 0 | 9 | 8/— | 4 | 7 | 8 |
| 12 | 2 | 0 | 9/0 | 0 | 0 | 8 |
| 13 | 7 | 0 | 9/— | — | — | — |
| 14 | 0 | 0 | 0/0 | — | — | — |
| 15 | 0 | 0 | 9/9 | 2 | 0 | 7 |
| 16 | 0 | 0 | 9/— | 0 | 0 | 0 |
| 17 | 0 | 0 | 8/8 | 0 | 8 | 8 |
| 18 | 6 | 0 | 9/— | 0 | 0 | 7 |
| 19 | 0 | 0 | 9/9 | 2 | 0 | 7 |
| 20 | 0 | 0 | 0/0 | — | — | 0 |
| 23 | 1 | 0 | 0/0 | — | — | 0 |

What is claimed is:
1. A compound of formula I

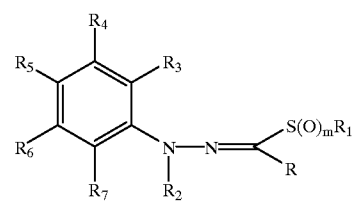

(I)

wherein
R is hydrogen,
  $C_1$–$C_{10}$alkyl optionally substituted with one or more halogen,
  $C_3$–$C_6$cycloalkyl,
  $C_1$–$C_4$alkoxy,
  $C_1$–$C_4$haloalkoxy,
  ($C_1$–$C_4$-alkyl)$SO_x$,
  ($C_1$–$C_4$haloalkyl)$SO_y$,
  phenyl optionally substituted with one to three halogen,
    $C_1$–$C_4$alkyl,
    $C_1$–$C_4$haloalkyl,
    $C_1$–$C_4$alkoxy,
    $C_1$–$C_4$haloalkoxy,
    ($C_1$–$C_4$alkyl)$SO_x$,
    ($C_1$–$C_4$haloalkyl)$SO_y$,
    $NO_2$ or CN groups, or phenoxy optionally substituted with one to three halogen,
  $C_1$–$C_4$alkyl,
  $C_1$–$C_4$haloalkyl,
  $C_1$–$C_4$alkoxy,
  $C_1$–$C_4$haloalkoxy,
  ($C_1$–$C_4$alkyl)$SO_x$,
  ($C_1$–$C_4$haloalkyl)$SO_y$,
  $NO_2$ or CN groups;
$C_3$–$C_{12}$cycloalkyl optionally substituted with one or more halogens,
  $C_1$–$C_6$alkyl,
  $C_1$–$C_4$haloalkyl,
  $C_1$–$C_4$alkoxy,
  $C_1$–$C_4$haloalkoxy,
  ($C_1$–$C_4$alkyl)$SO_x$,
  ($C_1$–$C_4$haloalkyl)$SO_x$,
  phenyl optionally substituted with one to three halogen,
    $C_1$–$C_4$alkyl
    $C_1$–$C_4$haloalkyl,
    $C_1$–$C_4$alkoxy,
    $C_1$–$C_4$haloalkoxy,
    $NO_2$ or CN groups, or
  phenoxy optionally substituted with one to three halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups; or
phenyl optionally substituted with one or more halogen,
  $C_1$–$C_4$alkyl,
  $C_1$–$C_4$haloalkyl,
  $C_1$–$C_4$alkoxy,
  $C_1$–$C_4$haloalkoxy,
  $NO_2$ or CN groups;
with the proviso that when R is an optionally substituted phenyl, then m must be 1 or 2;
$R_1$ is $R_{12}$;
  $C_1$–$C_{10}$alkyl optionally substituted with one or more halogen,
  hydroxy,
  phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups,
  $C_1$–$C_4$alkoxy,
  $C_1$–$C_4$haloalkoxy,
  ($C_1$–$C_4$alkyl)$SO_x$,
  $CONR_8R_9$,
  $CO_2R_{10}$,
  $R_{11}$,
  $R_{12}$,
  $C_3$–$C_6$cycloalkyl optionally substituted with one to three halogen,
    $C_1$–$C_4$alkyl,
    $C_1$–$C_4$ haloalkyl,
    $C_1$–$C_4$alkoxy,
    $C_1$–$C_4$haloalkoxy,
    $NO_2$ or CN groups,
  phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
  pyridyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups;
$C_2$–$C_{10}$alkenyl optionally substituted with one or more halogen,
  hydroxy,
  $C_1$–$C_4$alkoxy,
  ($C_1$–$C_4$alkyl)$SO_x$,
  $CONR_8R_9$,
  $CO_2R_{10}$,
  $R_{11}$,
  $R_{12}$,
  $C_3$–$C_6$cycloalkyl optionally substituted with one to three halogen,
    $C_1$–$C_4$alkyl,
    $C_1$–$C_4$halo-alkyl,
    $C_1$–$C_4$alkoxy,
    $C_1$–$C_4$haloalkoxy,
    $NO_2$ or CN groups,
  phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
  pyridyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups;
$C_2$–$C_{10}$alkynyl optionally substituted with one or more halogen,
  hydroxy,
  $C_1$–$C_4$alkoxy,
  ($C_1$–$C_4$alkyl)$SO_x$,
  $CONR_8R_9$,
  $CO_2R_{10}$,
  $R_{11}$,
  $R_{12}$,
  $C_3$–$C_6$cycloalkyl optionally substituted with one to three halogen,
    $C_1$–$C_4$alkyl,
    $C_1$–$C_4$halo-alkyl,
    $C_1$–$C_4$alkoxy,
    $C_1$–$C_4$haloalkoxy,
    $NO_2$ or CN groups,
  phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
  pyridyl optionally substituted with one or more halogen, $C_1$–$C_4$alkyl,
$C_1$–$C_4$haloalkyl,
$C_1$–$C_4$alkoxy,
$C_1$–$C_4$haloalkoxy,
$NO_2$ or CN groups; or
$C_3$–$C_{12}$cycloalkyl optionally substituted with one or more halogen,
hydroxy,
$C_1$–$C_4$alkoxy,
$(C_1$–$C_4$alkyl$)SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$R_2$ is hydrogen or $C_1$–$C_4$alkyl;
$R_3$, $R_4$, $R_5$, $R_6$, and $R_7$ are each independently hydrogen, halogen, CN, $NO_2$, $C_1$–$C_6$alkyl, $C_1$–$C_6$haloalkyl, $C_1$–$C_6$alkoxy, $C_1$–$C_6$haloalkoxy, or phenyl optionally substituted with one to three halogen, $C_1$–$C_4$alkyl, $C_1$–$C_4$haloalkyl, $C_1$–$C_4$alkoxy, $C_1$–$C_4$haloalkoxy, $(C_1$–$C_4$alkyl$)SO_x$, $(C_1$–$C_4$haloalkyl$)SO_y$, $NO_2$ or CN groups,
with the proviso that at least one of $R_3$, $R_4$, $R_5$, $R_6$ or $R_7$ must be phenyl optionally substituted with one to three halogen, $C_1$–$C_4$alkyl, $C_1$–$C_4$haloalkyl, $C_1$–$C_4$alkoxy, $C_1$–$C_4$haloalkoxy, $(C_1$–$C_4$alkyl$)SO_x$, $(C_1$–$C_4$haloalkyl$)SO_x$, $NO_2$ or CN groups;
x and y are each independently 0, 1 or 2;
m is an integer of 0, 1 or 2;
$R_8$, $R_9$ and $R_{10}$ are each independently hydrogen or $C_1$–$C_4$alkyl;

$R_{11}$ is $NR_{13}R_{14}$,

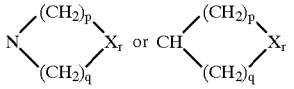

$R_{12}$ is

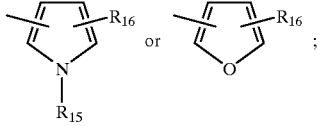

$R_{13}$, $R_{14}$, and $R_{15}$ are each independently hydrogen or $C_1$–$C_4$alkyl;
$R_{16}$ is hydrogen, halogen or $C_1$–$C_4$ alkyl;
X is O, S or $NR_{15}$;
r is an integer of 0 or 1;
p and q are each independently an integer of 0, 1, 2, or 3 with the proviso that only one of p, q, or r can be 0 and with the further proviso that the sum of p+q+r must be 4, 5 or 6; and
x is an integer of 0, 1 or 2; or
the acid addition salts thereof.

2. The compound according to claim 1 wherein $R_3$ and $R_7$ are each independently H or $C_1$–$C_6$alkoxy; and $R_4$ and $R_6$ are each independently H or phenyl optionally substituted with one or more halogen, $C_1$–$C_4$haloalkoxy, or $C_1$–$C_4$haloalkyl groups.

3. The compound according to claim 2 wherein R is $C_1$–$C_6$alkyl or $C_3$–$C_6$cycloalkyl optionally substituted with one to three halogens.

4. The compound according to claim 2, S-methyl-2,2-dimethylthiopropionate, 2-(4-methoxy-3-biphenylyl)-hydrazone; the S-oxide thereof; the S,S-dioxide thereof; or the acid addition salt thereof.

5. A method for the control of insect or acarid pests which comprises contacting said pests, their food supply, habitat or breeding grounds with a pesticidally effective amount of a compound of formula I

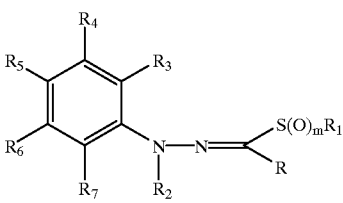

wherein
R is hydrogen,
$C_1$–$C_{10}$alkyl optionally substituted with one or more halogen,
$C_3$–$C_6$cycloalkyl,
$C_1$–$C_4$alkoxy,
$C_1$–$C_4$haloalkoxy,
$(C_1$–$C_4$-alkyl$)SO_x$,
$(C_1$–$C_4$haloalkyl$)SO_y$,
phenyl optionally substituted with one to three halogen,
$C_1$–$C_4$alkyl, $C_1$–$C_4$haloalkyl,
$C_1$–$C_4$alkoxy,
$C_1$–$C_4$haloalkoxy,
($C_1$–$C_4$alkyl)$SO_x$,
($C_1$–$C_4$haloalkyl)$SO_y$,
$NO_2$ or CN groups, or
phenoxy optionally substituted with one to three
halogen,
$C_1$–$C_4$alkyl,
$C_1$–$C_4$haloalkyl,
$C_1$–$C_4$alkoxy,
$C_1$–$C_4$haloalkoxy,
($C_1$–$C_4$alkyl)$SO_x$,
($C_1$–$C_4$haloalkyl)$SO_y$,
$NO_2$ or CN groups;
$C_3$–$C_{12}$cycloalkyl optionally substituted with one or
more halogens,
$C_1$–$C_6$alkyl,
$C_1$–$C_4$haloalkyl,
$C_1$–$C_4$alkoxy,
$C_1$–$C_4$haloalkoxy,
($C_1$–$C_4$alkyl)$SO_x$,
($C_1$–$C_4$haloalkyl)$SO_x$,
phenyl optionally substituted with one to three
halogen,
$C_1$–$C_4$alkyl
$C_1$–$C_4$haloalkyl,
$C_1$–$C_4$alkoxy,
$C_1$–$C_4$haloalkoxy,
$NO_2$ or CN groups, or
phenoxy optionally substituted with one to three
halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups; or
phenyl optionally substituted with one or more
halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
with the proviso that when R is an optionally substituted
phenyl, then m must be 1 or 2;
$R_1$ is $R_{12}$;
$C_1$–$C_{10}$alkyl optionally substituted with one or more
halogen,
hydroxy,
phenyl optionally substituted with one or more
halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups,
$C_1$–$C_4$alkoxy,
$C_1$–$C_4$haloalkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to
three halogen,
$C_1$–$C_4$alkyl, $C_1$–$C_4$ haloalkyl,
$C_1$–$C_4$alkoxy,
$C_1$–$C_4$haloalkoxy,
$NO_2$ or CN groups,
phenyl optionally substituted with one or more
halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more
halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$C_2$–$C_{10}$alkenyl optionally substituted with one or more
halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to
three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more
halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more
halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$C_2$–$C_{10}$alkynyl optionally substituted with one or more
halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to
three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more
halogen,
$C_1$–$C_4$alkyl, $C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups; or
$C_3$–$C_{12}$cycloalkyl optionally substituted with one or more halogen,
hydroxy,
$C_1$–$C_4$alkoxy,
$(C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$R_2$ is hydrogen or $C_1$–$C_4$alkyl;
$R_3$, $R_4$, $R_5$, $R_6$, and $R_7$ are each independently hydrogen, halogen, CN, $NO_2$, $C_1$–$C_6$alkyl, $C_1$–$C_6$haloalkyl, $C_1$–$C_6$alkoxy, $C_1$–$C_6$haloalkoxy, or phenyl optionally substituted with one to three halogen, $C_1$–$C_4$alkyl, $C_1$–$C_4$haloalkyl, $C_1$–$C_4$alkoxy, $C_1$–$C_4$haloalkoxy, $(C_1$–$C_4$alkyl)$SO_x$, $(C_1$–$C_4$haloalkyl)$SO_y$, $NO_2$ or CN groups,
with the proviso that at least one of $R_3$, $R_4$, $R_5$, $R_6$ or $R_7$ must be phenyl optionally substituted with one to three halogen, $C_1$–$C_4$alkyl, $C_1$–$C_4$haloalkyl, $C_1$–$C_4$alkoxy, $C_1$–$C_4$haloalkoxy, $(C_1$–$C_4$alkyl)$SO_x$, $(C_1$–$C_4$haloalkyl)$SO_x$, $NO_2$ or CN groups.

6. The method according to claim 5 wherein said pests are acarid pests.

7. The method according to claim 5 having a formula I compound wherein $R_3$ and $R_7$ are each independently H or $C_1$–$C_6$alkoxy; and $R_4$ and $R_6$ are each independently H or phenyl optionally substituted with one or more halogen, $C_1$–$C_4$haloalkoxy, or $C_1$–$C_4$haloalkyl groups.

8. The method according to claim 7 having a formula I compound wherein R is $C_1$–$C_6$alkyl or $C_3$–$C_6$cycloalkyl optionally substituted with one to three halogens.

9. The method according to claim 7 having the formula I compound, S-methyl-2,2-dimethylthiopropionate, 2-(4-methoxy-3-biphenylyl)-hydrazone; the S-oxide thereof; the S,S-dioxide thereof and the acid addition salt thereof.

10. A method for the protection of growing or harvested plants from attack or infestation by insect or acarid pests which comprises applying to the foliage of the plants, or to the soil or water in which they are growing, a pesticidally effective amount of a compound of formula I (I)

$$\text{structure with } R_4, R_5, R_3, R_6, R_7, R_2, \text{ and } S(O)_mR_1, R$$

wherein
R is hydrogen,
$C_1$–$C_{10}$alkyl optionally substituted with one or more halogen,
$C_3$–$C_6$cycloalkyl,
$C_1$–$C_4$alkoxy,
$C_1$–$C_4$haloalkoxy,
$(C_1$–$C_4$-alkyl)$SO_x$,
$(C_1$–$C_4$haloalkyl)$SO_y$,
phenyl optionally substituted with one to three halogen,
$C_1$–$C_4$alkyl,
$C_1$–$C_4$haloalkyl,
$C_1$–$C_4$alkoxy,
$C_1$–$C_4$haloalkoxy,
$(C_1$–$C_4$alkyl)$SO_x$,
$(C_1$–$C_4$haloalkyl)$SO_y$,
$NO_2$ or CN groups, or
phenoxy optionally substituted with one to three halogen,
$C_1$–$C_4$alkyl,
$C_1$–$C_4$haloalkyl,
$C_1$–$C_4$alkoxy,
$C_1$–$C_4$haloalkoxy,
$(C_1$–$C_4$alkyl)$SO_x$,
$(C_1$–$C_4$haloalkyl)$SO_y$,
$NO_2$ or CN groups;
$C_3$–$C_{12}$cycloalkyl optionally substituted with one or more halogens,
$C_1$–$C_6$alkyl,
$C_1$–$C_4$haloalkyl,
$C_1$–$C_4$alkoxy,
$C_1$–$C_4$haloalkoxy,
$(C_1$–$C_4$alkyl)$SO_x$,
$(C_1$–$C_4$haloalkyl)$SO_x$,
phenyl optionally substituted with one to three halogen, $C_1$–$C_4$alkyl
$C_1$–$C_4$haloalkyl,
$C_1$–$C_4$alkoxy,
$C_1$–$C_4$haloalkoxy,
$NO_2$ or CN groups, or
phenoxy optionally substituted with one to three halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups; or
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
with the proviso that when R is an optionally substituted phenyl, then m must be 1 or 2;
$R_1$ is $R_{12}$;
$C_1$–$C_{10}$alkyl optionally substituted with one or more halogen,
hydroxy,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups,
$C_1$–$C_4$alkoxy,
$C_1$–$C_4$haloalkoxy,
$(C_1$–$C_4$alkyl$)SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$ haloalkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$C_2$–$C_{10}$alkenyl optionally substituted with one or more halogen,
hydroxy,
$C_1$–$C_4$alkoxy,
$(C_1$–$C_4$alkyl$)SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$C_2$–$C_{10}$alkynyl optionally substituted with one or more halogen,
hydroxy,
$C_1$–$C_4$alkoxy,
$(C_1$–$C_4$alkyl$)SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$halo-alkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups; or
$C_3$–$C_{12}$cycloalkyl optionally substituted with one or more halogen,
hydroxy,
$C_1$–$C_4$alkoxy,
$(C_1$–$C_4$alkyl$)SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$halo-alkyl,
$C_1$–$C_4$alkoxy, C$_1$–C$_4$haloalkoxy,
NO$_2$ or CN groups,
phenyl optionally substituted with one or more halogen,
C$_1$–C$_4$alkyl,
C$_1$–C$_4$haloalkyl,
C$_1$–C$_4$alkoxy,
C$_1$–C$_4$haloalkoxy,
NO$_2$ or CN groups, or
pyridyl optionally substituted with one or more halogen,
C$_1$–C$_4$alkyl,
C$_1$–C$_4$haloalkyl,
C$_1$–C$_4$alkoxy,
C$_1$–C$_4$haloalkoxy,
NO$_2$ or CN groups;
phenyl optionally substituted with one or more halogen,
C$_1$–C$_4$alkyl,
C$_1$–C$_4$haloalkyl,
C$_1$–C$_4$alkoxy,
C$_1$–C$_4$haloalkoxy,
NO$_2$ or CN groups, or
pyridyl optionally substituted with one or more halogen,
C$_1$–C$_4$alkyl,
C$_1$–C$_4$haloalkyl,
C$_1$–C$_4$alkoxy,
C$_1$–C$_4$haloalkoxy,
NO$_2$ or CN groups;
R$_2$ is hydrogen or C$_1$–C$_4$alkyl;
R$_3$, R$_4$, R$_5$, R$_6$, and R$_7$ are each independently hydrogen, halogen, CN, NO$_2$, C$_1$–C$_6$alkyl, C$_1$–C$_6$haloalkyl, C$_1$–C$_6$alkoxy, C$_1$–C$_6$haloalkoxy, or phenyl optionally substituted with one to three halogen, C$_1$–C$_4$alkyl, C$_1$–C$_4$haloalkyl, C$_1$–C$_4$alkoxy, C$_1$–C$_4$haloalkoxy, (C$_1$–C$_4$alkyl)SO$_x$, (C$_1$–C$_4$haloalkyl)SO$_y$, NO$_2$ or CN groups,
with the proviso that at least one of R$_3$, R$_4$, R$_5$, R$_6$ or R$_7$ must be phenyl optionally substituted with one to three halogen, C$_1$–C$_4$alkyl, C$_1$–C$_4$haloalkyl, C$_1$–C$_4$alkoxy, C$_1$–C$_4$haloalkoxy, (C$_1$–C$_4$alkyl)SO$_x$, (C$_1$–C$_4$haloalkyl)SO$_x$, NO$_2$ or CN groups.

11. The method according to claim 10 wherein said pests are acarid pests.

12. The method according to claim 10 wherein the compound of formula I is applied in a concentration of about 10 ppm to 10,000 ppm.

13. The method according to claim 10 wherein the compound of formula I is applied in a concentration in about 100 ppm to 5,000 ppm.

14. A composition for controlling insect or acarid pests which comprises an agriculturally acceptable carrier and a pesticidally effective amount of a compound of formula I

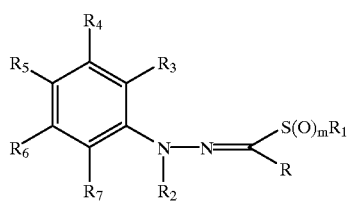

(I)

wherein
R is hydrogen,
C$_1$–C$_{10}$alkyl optionally substituted with one or more halogen,
C$_3$–C$_6$cycloalkyl,
C$_1$–C$_4$alkoxy,
C$_1$–C$_4$haloalkoxy,
(C$_1$–C$_4$-alkyl)SO$_x$,
(C$_1$–C$_4$haloalkyl)SO$_y$,
phenyl optionally substituted with one to three halogen,
C$_1$–C$_4$alkyl,
C$_1$–C$_4$haloalkyl,
C$_1$–C$_4$alkoxy,
C$_1$–C$_4$haloalkoxy,
(C$_1$–C$_4$alkyl)SO$_x$,
(C$_1$–C$_4$haloalkyl)SO$_y$,
NO$_2$ or CN groups, or
phenoxy optionally substituted with one to three halogen,
C$_1$–C$_4$alkyl,
C$_1$–C$_4$haloalkyl,
C$_1$–C$_4$alkoxy,
C$_1$–C$_4$haloalkoxy,
(C$_1$–C$_4$alkyl)SO$_x$,
(C$_1$–C$_4$haloalkyl)SO$_y$,
NO$_2$ or CN groups;
C$_3$–C$_{12}$cycloalkyl optionally substituted with one or more halogens,
C$_1$–C$_6$alkyl,
C$_1$–C$_4$haloalkyl,
C$_1$–C$_4$alkoxy,
C$_1$–C$_4$haloalkoxy,
(C$_1$–C$_4$alkyl)SO$_x$,
(C$_1$–C$_4$haloalkyl)SO$_x$,
phenyl optionally substituted with one to three halogen,
C$_1$–C$_4$alkyl
C$_1$–C$_4$haloalkyl,
C$_1$–C$_4$alkoxy,
C$_1$–C$_4$haloalkoxy,
NO$_2$ or CN groups, or
phenoxy optionally substituted with one to three halogen,
C$_1$–C$_4$alkyl,
C$_1$–C$_4$haloalkyl,
C$_1$–C$_4$alkoxy,
C$_1$–C$_4$haloalkoxy,
NO$_2$ or CN groups; or
phenyl optionally substituted with one or more halogen,
C$_1$–C$_4$alkyl,
C$_1$–C$_4$haloalkyl,
C$_1$–C$_4$alkoxy,
C$_1$–C$_4$haloalkoxy,
NO$_2$ or CN groups;
with the proviso that when R is an optionally substituted phenyl, then m must be 1 or 2;
R$_1$ is R$_{12}$;
C$_1$–C$_{10}$alkyl optionally substituted with one or more halogen,
hydroxy,
phenyl optionally substituted with one or more halogen,
C$_1$–C$_4$alkyl,
C$_1$–C$_4$haloalkyl,
C$_1$–C$_4$alkoxy,
C$_1$–C$_4$haloalkoxy,
NO$_2$ or CN groups, $C_1$–$C_4$alkoxy,
$C_1$–$C_4$haloalkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
    $C_1$–$C_4$alkyl,
    $C_1$–$C_4$ haloalkyl,
    $C_1$–$C_4$alkoxy,
    $C_1$–$C_4$haloalkoxy,
    $NO_2$ or CN groups,
phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
pyridyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups;
$C_2$–$C_{10}$alkenyl optionally substituted with one or more halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
    $C_1$–$C_4$alkyl,
    $C_1$–$C_4$halo-alkyl,
    $C_1$–$C_4$alkoxy,
    $C_1$–$C_4$haloalkoxy,
    $NO_2$ or CN groups,
phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
pyridyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups;
$C_2$–$C_{10}$alkynyl optionally substituted with one or more halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
    $C_1$–$C_4$alkyl,
    $C_1$–$C_4$halo-alkyl,
    $C_1$–$C_4$alkoxy,
    $C_1$–$C_4$haloalkoxy,
    $NO_2$ or CN groups,
phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
pyridyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups; or
$C_3$–$C_{12}$cycloalkyl optionally substituted with one or more halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
    $C_1$–$C_4$alkyl,
    $C_1$–$C_4$halo-alkyl,
    $C_1$–$C_4$alkoxy,
    $C_1$–$C_4$haloalkoxy,
    $NO_2$ or CN groups,
phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
pyridyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups;
phenyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups, or
pyridyl optionally substituted with one or more halogen,
    $C_1$–$C_4$alkyl,
    $C_1$–$C_4$haloalkyl,
    $C_1$–$C_4$alkoxy,
    $C_1$–$C_4$haloalkoxy,
    $NO_2$ or CN groups;
$R_2$ is hydrogen or $C_1$–$C_4$alkyl;
$R_3$, $R_4$, $R_5$, $R_6$, and $R_7$ are each independently hydrogen, halogen, CN, $NO_2$, $C_1$–$C_6$alkyl, $C_1$–$C_6$haloalkyl, $C_1$–$C_6$alkoxy, $C_1$–$C_6$haloalkoxy, or phenyl optionally substituted with one to three halogen, $C_1$–$C_4$alkyl, $C_1$–$C_4$haloalkyl, $C_1$–$C_4$alkoxy, $C_1$–$C_4$haloalkoxy, ($C_1$–$C_4$alkyl)$SO_x$, ($C_1$–$C_4$haloalkyl)$SO_y$, $NO_2$ or CN groups, with the proviso that at least one of $R_3$, $R_4$, $R_5$, $R_6$ or $R_7$ must be phenyl optionally substituted with one to three halogen, $C_1$–$C_4$alkyl, $C_1$–$C_4$haloalkyl, $C_1$–$C_4$alkoxy, $C_1$–$C_4$haloalkoxy, ($C_1$–$C_4$alkyl)$SO_x$, ($C_1$–$C_4$haloalkyl)$SO_x$, $NO_2$ or CN groups.

15. The composition according to claim 14 wherein $R_3$ and $R_7$ are each independently H or $C_1$–$C_6$alkoxy; and $R_4$ and $R_6$ are each independently H or phenyl optionally substituted with one or more halogen, $C_1$–$C_4$haloalkoxy, or $C_1$–$C_4$haloalkyl groups.

16. The composition according to claim 14 wherein R is $C_1$–$C_6$alkyl or $C_3$–$C_6$cycloalkyl optionally substituted with one to three halogens.

17. The composition according to claim 15 wherein the compound of formula I is 5-methyl-2,2-dimethylthiopropionate(4-methoxy-3-biphenylyl)hydrazone; the S-oxide thereof; the S,S-dioxide thereof; or the acid addition salt thereof.

18. A process for the preparation of a compound of formula I

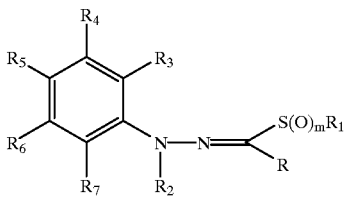

(I)

wherein
R is hydrogen,
$C_1$–$C_{10}$alkyl optionally substituted with one or more halogen,
$C_3$–$C_6$cycloalkyl,
$C_1$–$C_4$alkoxy,
$C_1$–$C_4$haloalkoxy,
($C_1$–$C_4$-alkyl)$SO_x$,
($C_1$–$C_4$haloalkyl)$SO_y$,
phenyl optionally substituted with one to three halogen,
$C_1$–$C_4$alkyl,
$C_1$–$C_4$haloalkyl,
$C_1$–$C_4$alkoxy,
$C_1$–$C_4$haloalkoxy,
($C_1$–$C_4$alkyl)$SO_x$,
($C_1$–$C_4$haloalkyl)$SO_y$,
$NO_2$ or CN groups, or
phenoxy optionally substituted with one to three halogen,
$C_1$–$C_4$alkyl,
$C_1$–$C_4$haloalkyl,
$C_1$–$C_4$alkoxy,
$C_1$–$C_4$haloalkoxy,
($C_1$–$C_4$alkyl)$SO_x$,
($C_1$–$C_4$haloalkyl)$SO_y$,
$NO_2$ or CN groups;
$C_3$–$C_{12}$cycloalkyl optionally substituted with one or more halogens,
$C_1$–$C_6$alkyl,
$C_1$–$C_4$haloalkyl,
$C_1$–$C_4$alkoxy,
$C_1$–$C_4$haloalkoxy,
($C_1$–$C_4$alkyl)$SO_x$,
($C_1$–$C_4$haloalkyl)$SO_x$,
phenyl optionally substituted with one to three halogen,
$C_1$–$C_4$alkyl
$C_1$–$C_4$haloalkyl,
$C_1$–$C_4$alkoxy,
$C_1$–$C_4$haloalkoxy,
$NO_2$ or CN groups, or
phenoxy optionally substituted with one to three halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups; or
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
with the proviso that when R is an optionally substituted phenyl, then m must be 1 or 2;
$R_1$ is $R_{12}$;
$C_1$–$C_{10}$alkyl optionally substituted with one or more halogen,
hydroxy,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups,
$C_1$–$C_4$alkoxy,
$C_1$–$C_4$haloalkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
$C_1$–$C_4$alkyl,
$C_1$–$C_4$ haloalkyl,
$C_1$–$C_4$alkoxy,
$C_1$–$C_4$haloalkoxy,
$NO_2$ or CN groups,
phenyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups, or
pyridyl optionally substituted with one or more halogen,
$C_1$–$C_4$alkyl,
$C_1$–$C_4$haloalkyl,
$C_1$–$C_4$alkoxy,
$C_1$–$C_4$haloalkoxy,
$NO_2$ or CN groups;
$C_2$–$C_{10}$alkenyl optionally substituted with one or more halogen, hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
   $C_1$–$C_4$alkyl,
   $C_1$–$C_4$halo-alkyl,
   $C_1$–$C_4$alkoxy,
   $C_1$–$C_4$haloalkoxy,
   $NO_2$ or CN groups,
phenyl optionally substituted with one or more halogen,
   $C_1$–$C_4$alkyl,
   $C_1$–$C_4$haloalkyl,
   $C_1$–$C_4$alkoxy,
   $C_1$–$C_4$haloalkoxy,
   $NO_2$ or CN groups, or
pyridyl optionally substituted with one or more halogen,
   $C_1$–$C_4$alkyl,
   $C_1$–$C_4$haloalkyl,
   $C_1$–$C_4$alkoxy,
   $C_1$–$C_4$haloalkoxy,
   $NO_2$ or CN groups;
$C_2$–$C_{10}$alkynyl optionally substituted with one or more halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
   $C_1$–$C_4$alkyl,
   $C_1$–$C_4$halo-alkyl,
   $C_1$–$C_4$alkoxy,
   $C_1$–$C_4$haloalkoxy,
   $NO_2$ or CN groups,
phenyl optionally substituted with one or more halogen,
   $C_1$–$C_4$alkyl,
   $C_1$–$C_4$haloalkyl,
   $C_1$–$C_4$alkoxy,
   $C_1$–$C_4$haloalkoxy,
   $NO_2$ or CN groups, or
pyridyl optionally substituted with one or more halogen,
   $C_1$–$C_4$alkyl,
   $C_1$–$C_4$haloalkyl,
   $C_1$–$C_4$alkoxy,
   $C_1$–$C_4$haloalkoxy,
   $NO_2$ or CN groups; or
$C_3$–$C_{12}$cycloalkyl optionally substituted with one or more halogen,
hydroxy,
$C_1$–$C_4$alkoxy,
($C_1$–$C_4$alkyl)$SO_x$,
$CONR_8R_9$,
$CO_2R_{10}$,
$R_{11}$,
$R_{12}$,
$C_3$–$C_6$cycloalkyl optionally substituted with one to three halogen,
   $C_1$–$C_4$alkyl,
   $C_1$–$C_4$halo-alkyl,
   $C_1$–$C_4$alkoxy,
   $C_1$–$C_4$haloalkoxy,
   $NO_2$ or CN groups,
phenyl optionally substituted with one or more halogen,
   $C_1$–$C_4$alkyl,
   $C_1$–$C_4$haloalkyl,
   $C_1$–$C_4$alkoxy,
   $C_1$–$C_4$haloalkoxy,
   $NO_2$ or CN groups, or
pyridyl optionally substituted with one or more halogen,
   $C_1$–$C_4$alkyl,
   $C_1$–$C_4$haloalkyl,
   $C_1$–$C_4$alkoxy,
   $C_1$–$C_4$haloalkoxy,
   $NO_2$ or CN groups;
phenyl optionally substituted with one or more halogen,
   $C_1$–$C_4$alkyl,
   $C_1$–$C_4$haloalkyl,
   $C_1$–$C_4$alkoxy,
   $C_1$–$C_4$haloalkoxy,
   $NO_2$ or CN groups, or
pyridyl optionally substituted with one or more halogen,
   $C_1$–$C_4$alkyl,
   $C_1$–$C_4$haloalkyl,
   $C_1$–$C_4$alkoxy,
   $C_1$–$C_4$haloalkoxy,
   $NO_2$ or CN groups;

$R_2$ is hydrogen or $C_1$–$C_4$alkyl;

$R_3$, $R_4$, $R_5$, $R_6$, and $R_7$ are each independently hydrogen, halogen, CN, $NO_2$, $C_1$–$C_6$alkyl, $C_1$–$C_6$haloalkyl, $C_1$–$C_6$alkoxy, $C_1$–$C_6$haloalkoxy, or phenyl optionally substituted with one to three halogen, $C_1$–$C_4$alkyl, $C_1$–$C_4$haloalkyl, $C_1$–$C_4$alkoxy, $C_1$–$C_4$haloalkoxy, ($C_1$–$C_4$alkyl)$SO_x$, ($C_1$–$C_4$haloalkyl)$SO_y$, $NO_2$ or CN groups, with the proviso that at least one of $R_3$, $R_4$, $R_5$, $R_6$ or $R_7$ must be phenyl optionally substituted with one to three halogen, $C_1$–$C_4$alkyl, $C_1$–$C_4$haloalkyl, $C_1$–$C_4$alkoxy, $C_1$–$C_4$haloalkoxy, ($C_1$–$C_4$alkyl)$SO_x$, ($C_1$–$C_4$haloalkyl) $SO_x$, $NO_2$ or CN groups;

x and y are each independently 0, 1 or 2;

m is an integer of 0, 1 or 2;

$R_8$, $R_9$ and $R_{10}$ are each independently hydrogen or $C_1$–$C_4$alkyl;

$R_{11}$ is $NR_{13}R_{14}$,

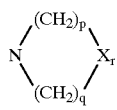  or  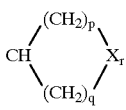

$R_{12}$ is

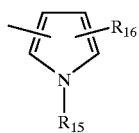  or  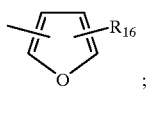 ;

$R_{13}$, $R_{14}$, and $R_{15}$ and are each independently hydrogen or $C_1$–$C_4$alkyl;

$R_{16}$ is hydrogen, halogen or $C_1$–$C_4$ alkyl;

X is O, S or $NR_{15}$;

r is an integer of 0 or 1;

p and q are each independently an integer of 0, 1, 2, or 3 with the proviso that only one of p, q, or r can be 0 and with the further proviso that the sum of p+q+r must be 4, 5 or 6; and x is an integer of 0, 1 or 2;

which process comprises reacting a compound of formula II

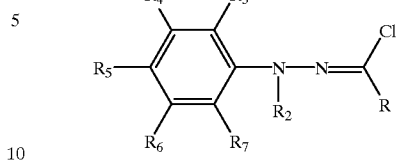 (II)

wherein $X^1$ is halogen and R, $R_2$, $R_3$, $R_4$, $R_5$, $R_6$, and $R_7$ are as hereinbefore defined, with at least one molar equivalent of a mercaptan of formula III

HS—$R_1$ (III)

wherein $R_1$ is as hereinbefore defined, in the presence of a base, optionally in the presence of a solvent, to form the compound of formula I wherein m is 0, optionally reacting the compound of formula I wherein m is 0 with one or more molar equivalents of an oxidizing reagent to form a compound of formula I wherein m is 1 or 2.

* * * * *